(12) United States Patent
Fright et al.

(10) Patent No.: US 9,377,295 B2
(45) Date of Patent: Jun. 28, 2016

(54) METHOD OF MONITORING A SURFACE FEATURE AND APPARATUS THEREFOR

(71) Applicants: William Richard Fright, Christchurch (NZ); Mark Arthur Nixon, Christchurch (NZ); Bruce Clinton McCallum, Lyttelton (NZ); James Telford George Preddey, Einsiedeln (CH)

(72) Inventors: William Richard Fright, Christchurch (NZ); Mark Arthur Nixon, Christchurch (NZ); Bruce Clinton McCallum, Lyttelton (NZ); James Telford George Preddey, Einsiedeln (CH)

(73) Assignee: ARANZ HEALTHCARE LIMITED, Christchurch (NZ)

( * ) Notice: Subject to any disclaimer, the term of this patent is extended or adjusted under 35 U.S.C. 154(b) by 0 days.

(21) Appl. No.: 14/272,719

(22) Filed: May 8, 2014

(65) Prior Publication Data

US 2014/0243619 A1    Aug. 28, 2014

Related U.S. Application Data

(63) Continuation of application No. 12/083,491, filed as application No. PCT/NZ2006/000262 on Oct. 13, 2006, now Pat. No. 8,755,053.

(30) Foreign Application Priority Data

Oct. 14, 2005 (NZ) ........................................ 543003

(51) Int. Cl.
| | |
|---|---|
| G01B 11/24 | (2006.01) |
| G01B 11/00 | (2006.01) |
| A61B 5/107 | (2006.01) |
| A61B 5/00 | (2006.01) |
| G06T 7/00 | (2006.01) |
| A61B 5/01 | (2006.01) |
| A61B 5/145 | (2006.01) |
| A61B 8/08 | (2006.01) |
| G01B 11/02 | (2006.01) |

(52) U.S. Cl.
CPC ............ *G01B 11/002* (2013.01); *A61B 5/0013* (2013.01); *A61B 5/0022* (2013.01); *A61B 5/0077* (2013.01); *A61B 5/01* (2013.01); *A61B 5/1077* (2013.01); *A61B 5/14539* (2013.01); *A61B 5/445* (2013.01); *A61B 5/7275* (2013.01); *A61B 5/7282* (2013.01); *A61B 5/746* (2013.01); *A61B 8/488* (2013.01); *G01B 11/02* (2013.01); *G06T 7/0004* (2013.01)

(58) Field of Classification Search
None
See application file for complete search history.

(56) References Cited

U.S. PATENT DOCUMENTS

| | | | | |
|---|---|---|---|---|
| 5,561,526 A * | 10/1996 | Huber et al. | ................... | 356/604 |
| 6,091,995 A * | 7/2000 | Ingle et al. | ..................... | 607/138 |
| 6,101,408 A * | 8/2000 | Craine et al. | .................. | 600/425 |
| 6,413,212 B1 * | 7/2002 | Raab | .............................. | 600/300 |
| 2003/0229514 A2 * | 12/2003 | Brown | .............................. | 705/2 |
| 2004/0080497 A1 * | 4/2004 | Enmei | ......................... | 345/174 |
| 2005/0012817 A1 * | 1/2005 | Hampapur et al. | ........... | 348/143 |
| 2006/0293613 A1 * | 12/2006 | Fatehi et al. | .................. | 600/587 |
| 2010/0111387 A1 * | 5/2010 | Christiansen, II et al. | .... | 382/128 |

* cited by examiner

*Primary Examiner* — Peling Shaw
(74) *Attorney, Agent, or Firm* — Blakely Sokoloff Taylor & Zafman LLP

(57) ABSTRACT

Dimensions of a surface feature are determined by capturing an image of the surface feature and determining a scale associated with the image. Structured light may be projected onto the surface, such that the position of structured light in the captured image allows determination of scale. A non-planar surface may be unwrapped. The surface may alternatively be projected into a plane to correct for the scene being tilted with respect to the camera axis. A border of the surface feature may be input manually by a user. An apparatus and system for implementing the method are also disclosed.

26 Claims, 7 Drawing Sheets

METHOD OF MONITORING A SURFACE FEATURE AND APPARATUS THEREFOR

CROSS REFERENCE TO RELATED APPLICATION

This application is a continuation of pending U.S. patent application Ser. No. 12/083,491 filed May 11, 2009, now U.S. Pat. No. 8,755,053 issued Jun. 17, 2014, entitled, "A METHOD FOR MONITORING A SURFACE FEATURE AND APPARATUS THEREFOR", which is a national stage of International Application No. PCT/NZ2006/00262, filed Oct. 13, 2006.

FIELD OF THE INVENTION

The invention relates to a method of monitoring a surface feature and an apparatus for performing such monitoring. The method and apparatus may find application in a wide range of fields from industrial applications through to medical or veterinary applications such as monitoring dermatological surface features such as wounds, ulcers, sores, lesions, tumours, bruises, burns, psoriasis, keloids, skin cancers, erythema etc.

BACKGROUND TO THE INVENTION

Various techniques have been used to monitor wounds, ulcers, sores, lesions, tumours etc. (herein referred to collectively as "wounds") both within hospitals and outside hospitals (e.g. domiciliary based care, primary care facilities etc.). Typically these wounds are concave and up to about 250 millimeters across. Manual techniques are typically labour-intensive and require examination and contact by skilled personnel. Such measurements may be inaccurate and there may be significant variation between measurements made by different personnel. Further, these approaches may not preserve any visual record for review by an expert or for subsequent comparison.

A number of techniques for the automated monitoring of wounds have been proposed; see for example U.S. Pat. No. 6,101,408, U.S. Pat. No. 6,873,340, U.S. Pat. No. 4,535,782 and U.S. Pat. No. 5,967,979. A common approach is to place a reference object next to the wound and determine the size of the wound utilising the scale of the reference object. It is often undesirable to place a reference object near to a wound and this requires an additional cumbersome step for a user and risks contamination of the wound. Further, when the target is not in the plane of the wound, or if the wound is not planar, there will be errors in any area calculation.

WO 2006/078902 discloses a system in which the scale of a captured image is determined using a laser triangulation sensor. The distance of the camera from a patient's skin is determined using the position of a laser spot in the image. Only a single laser spot is used and the laser is used only in a simple distance measurement.

Systems utilising stereoscopic vision and auto-mated boundary determination are known but they are expensive, complex, bulky and require significant computational power. Further, automated identification of the boundary of a wound-may be inaccurate and variable. U.S. Pat. No. 6,567,682 and US2005/0084176, now U.S. Pat. No. 7,450,783 issued Nov. 11, 2008, use stereoscopic techniques and automated wound boundary determination requiring intensive processing and bulky equipment.

Other systems, such as that described in US2004/0136579, now U.S. Pat. No. 7,248,724 issued Jul. 24, 2007, require the camera always to be positioned with a guide against the patient's skin. While this consistently positions the camera a desired distance from the surface to be photographed and therefore sets the scale of the image, it is unwieldy and requires undesirable contact with the skin, risking contamination of the wound.

US2005/0027567 (U.S. application Ser. No. 10/900,911, now abandoned) discloses a system in which a medical professional may enter patient information into a portable computing device. A nurse may also photograph the patient's wounds, these photographs becoming part of the patient's record. However, use of this image data is limited and the computing device is effectively used simply to allow notes to be taken.

It is an object of the invention to provide a simple, inexpensive and repeatable method that does not require a scale reference object to be employed and that may be performed at remote locations or to at least provide the public with a useful choice. It is a further object of the invention to provide an apparatus that is simple, portable, inexpensive and easy to use or which at least provides the public with a useful choice.

SUMMARY OF THE INVENTION

There is thus provided a method of producing a projection of a non-planar surface feature comprising:
  a. projecting structured light onto the surface feature;
  b. capturing an image including the surface feature;
  c. determining the three-dimensional coordinates of structured light elements within the image; and
  d. unwrapping the image based on the three-dimensional coordinates of the structured light elements to produce a planar projection of the surface feature.

According to a further embodiment there is provided a method of determining the area of a non-planar surface feature comprising:
  a. projecting structured light onto the surface feature;
  b. capturing an image including the surface feature;
  c. determining the three-dimensional coordinates of structured light elements within the image;
  d. determining scale attributes for regions of the image on the basis of the three-dimensional coordinates of the structured light elements; and
  e. determining the area of the surface feature by scaling regions of the surface feature based on the scale attributes.

According to another embodiment there is provided a method of producing a projection of a surface feature comprising:
  a. capturing an image of a surface feature;
  b. determining from the image the coordinates of a plurality of points of the surface feature in three-dimensional space;
  c. determining a plane in which at least a subset of the coordinates lie; and
  d. projecting the image onto the plane to produce a transformed image.

According to a further embodiment there is provided a method of determining at least one dimension of a surface feature, including:
  a. capturing an image including a surface feature;
  b. determining a scale associated with the image;
  c. manually inputting at least part of an outline of the surface feature; and
  d. determining at least one dimension of the surface feature using the manually input outline data.

According to another embodiment there is provided an apparatus including:
a. a camera for capturing an image including a surface feature; and
b. a portable computing device including:
  i. a display configured to display the image and to allow a user to manually input at least part of an outline of the surface feature; and
  ii. a processor configured to determine a scale associated with the image and to determine at least one dimension of the surface feature using the manually input outline data.

According to a further embodiment there is provided a portable apparatus including:
a. a camera for capturing an image of a surface feature;
b. a portable computing device including a processor adapted to determine a scale associated with the image; and
c. a positioning module allowing the position of the apparatus to be determined.

According to another embodiment there is provided a healthcare apparatus including:
a. a camera for capturing an image of a surface feature on a patient;
b. one or more auxiliary sensors for determining a physical or chemical parameter associated with the patient; and
c. a portable computing device configured to receive image data from the camera and output from the auxiliary sensors, including a processor adapted to determine a scale associated with the image.

According to a further embodiment there is provided an apparatus including:
a. a camera for capturing an image including a surface feature; and
b. one or more structured light projectors configured to project structured light onto the surface, the structured light including two or more structured light components, each projected at a different angle to the camera's optical axis.

DRAWINGS

The invention will now be described by way of example with reference to possible embodiments thereof as shown in the accompanying figures in which.

DETAILED DESCRIPTION

Figure 1:
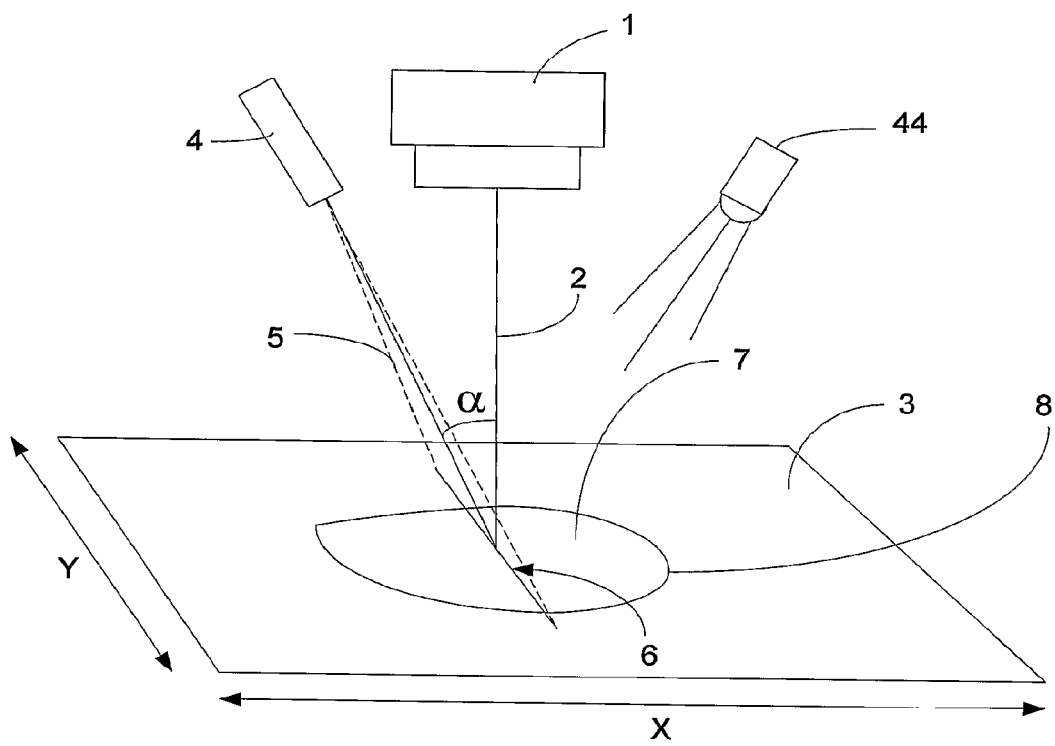
FIG. 1 shows the principle of operation of an apparatus according to one embodiment.

Referring to FIG. 1 the general principle of operation of a first embodiment of the invention will be described. A camera 1 has an optical axis 2 and an image capture region 3. Laser 4 is disposed in a fixed angular relationship to optical axis 2 so that the fan beam 5 is disposed at angle $\alpha$ to optical axis 2. In this embodiment laser 4 generates a single stripe 6. Alternatively a laser projecting a single dot could be used. The camera 1 is preferably a high resolution digital colour camera. Optionally, an illumination means (such as a white LED 44 for low power applications) can be used to give relatively constant background lighting.

In use the assembly of camera 1 and laser 4 is directed so that optical axis 2 is aligned with the central region of wound 7. Laser 4 projects stripe 6 across wound 7 and the image is captured by camera 1. It will be appreciated that due to the fixed angular relationship of the laser fan beam 5 and the optical axis 2 that the distance of points of stripe 6 from camera 1 may be determined: the distance of points of stripe 6 along the x-axis shown in FIG. 1 is directly related to the distance of the point from camera 1.

In a first embodiment the assembly of camera 1 and laser 4 may be positioned above wound 7 so that stripe 6 is aligned with optical axis 2. This may be achieved by aligning cross hairs (or a dot) in the centre of a display screen displaying the image with the centre of wound 7 and stripe 6. In this way the camera is positioned a known distance away from the centre of wound 7 and so a scale can be determined.

The area of a wound may be calculated by calculating the pixel area of wound 7 from a captured image and multiplying by a known scaling factor. This technique may be effective where camera 1 can be oriented normal to the wound 7 and where wound 7 is generally planar. This technique offers a simple solution in such cases. However, many wounds are not generally planar and images may be taken at an oblique angle. In such cases this approach may not provide sufficient accuracy and repeatability due to the camera axis not being perpendicular to the wound and significant variation in the distance from the camera to the wound from that assumed.

Figure 2:
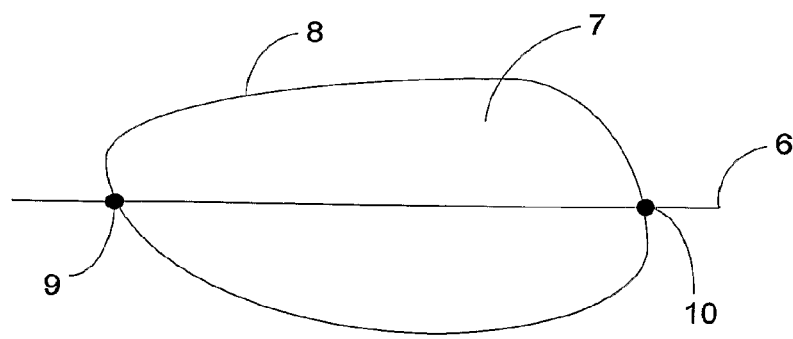
FIG. 2 shows an image of a surface feature with a single stripe projected onto the surface feature.

In a second embodiment an image may be captured in the same fashion except that the stripe need not be aligned with the optical axis of the camera. An image as shown in FIG. 2 may be obtained. Points 9 and 10, where the outline 8 of wound 7 intersects stripe 6, may be used to calculate scale. From the locations of points 9 and 10 in the image 3 their corresponding (x, y, z) coordinates can be obtained using the known relationship of the laser-camera system. Thus a scale factor may be determined based on the x,y,z coordinates of points 9 and 10 to scale the area 7 to produce a scaled value. Whilst this technique does not require a user to align the stripe with the optical axis it still suffers from the limitations of the technique described above.

Figure 3A:
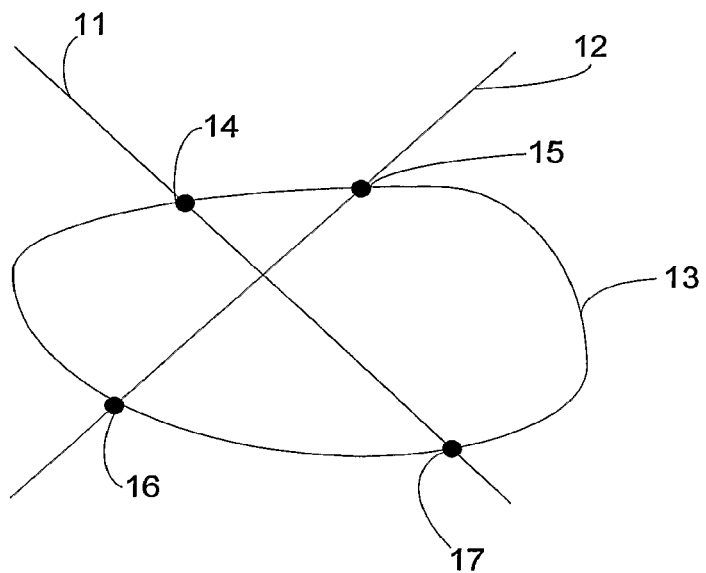
FIG. 3a shows an image of a surface feature with cross hairs projected onto the surface feature.

In one embodiment laser 4 projects structured light in the form of laser cross hairs onto the image capture area. An image captured according to this embodiment is shown in FIG. 3a. The laser stripes 11 and 12 captured in the image may be identified automatically based on colour, light intensity etc. The outline 13 is preferably user defined by drawing the outline on a touch display screen displaying the image. The image points 14, 15, 16 and 17 where cross hairs 11 and 12 intersect with outline 13 may be automatically determined. From these points their corresponding (x, y, z) coordinates can be obtained as above. These three-dimensional coordinates may be utilised to determine the best-fit plane through all points. The best-fit plane will generally be the plane having the minimum sum of squared orthogonal distances from the points to the plane. The image may then be projected onto this plane using, for example, an affine transformation. The resulting image is now scaled linearly and orthogonally. The area within outline 13 may then be calculated from this transformed image. Any number of laser stripes may be used and these stripes may intersect with each other or not.

This approach has the advantage that it provides correction where an image is not taken normal to a wound. Determining the area within a two dimensional outline rather than in three dimensional space also reduces the computational load.

Figure 3B:
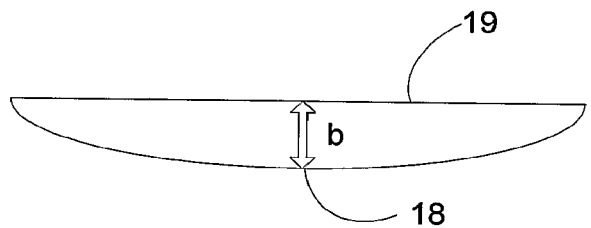
FIG. 3b shows a cross-sectional view of a wound.

A wound depth measurement may also be derived as will be explained in connection with FIG. 3*b*. The point 18 of greatest depth b from best-fit plane 19 may be determined iteratively or by other methods. This may be determined for an individual point along one of the cross hairs 11,12 or for a group of points.

Utilising this information standard wound measurements may be made. The so-called "Kundin area" may be calculated by obtaining the maximum linear dimension of the wound and the short axis (orthogonal to the long axis) of the outline and multiplying the product of these measurements by $\pi/4$. The so-called "Kundin volume" may be calculated from the product of the two diameters, the maximum depth and a factor of 0.327. The dimensions may be determined and the volume calculated by a local processor. Various other algorithms may be used to calculate wound volume as appropriate for the circumstances.

Figure 4:
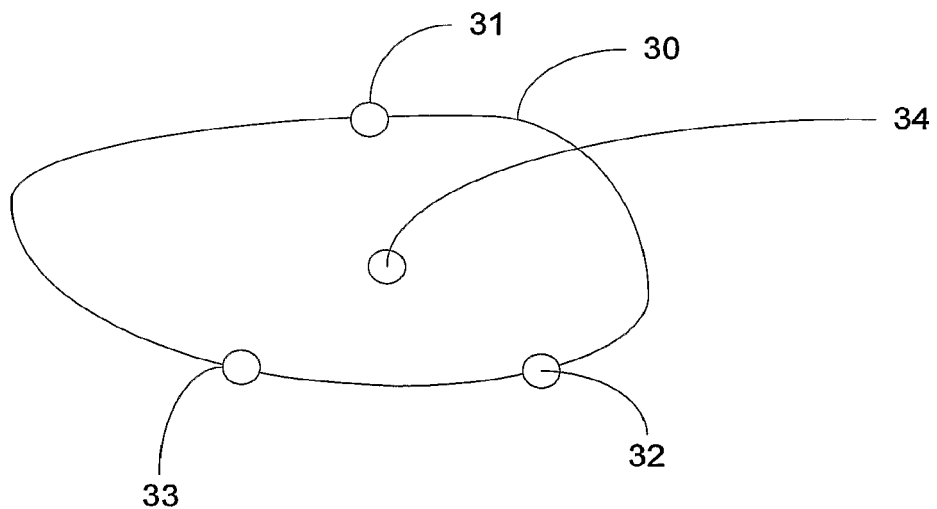
FIG. 4 shows an image of a surface feature with a series of dots projected onto the surface feature.

Referring now to FIG. 4 another implementation is shown. In this case a series of three laser dots 31, 32 and 33 are projected instead of one or more laser stripe. The laser dots are projected in a diverging pattern so that as the device is moved towards or away from the surface feature the spacing between the dots may be scaled so that they may be aligned with the outline of the wound 30. This approach has the advantage that the intersection between the stripes and the wound outline does not need to be determined as in previous embodiment. Further, the plane passing through the three points may be easily calculated. A further point 34 may be provided for depth calculation. Point 34 will preferably be placed at the position of maximum wound depth.

The outline of the wound may be determined utilising image processing techniques. However, the results of such techniques may be variable depending upon image quality, available processing capacity and the optical characteristics of the wound. According to a preferred embodiment the outline is input by a user.

Figure 5:
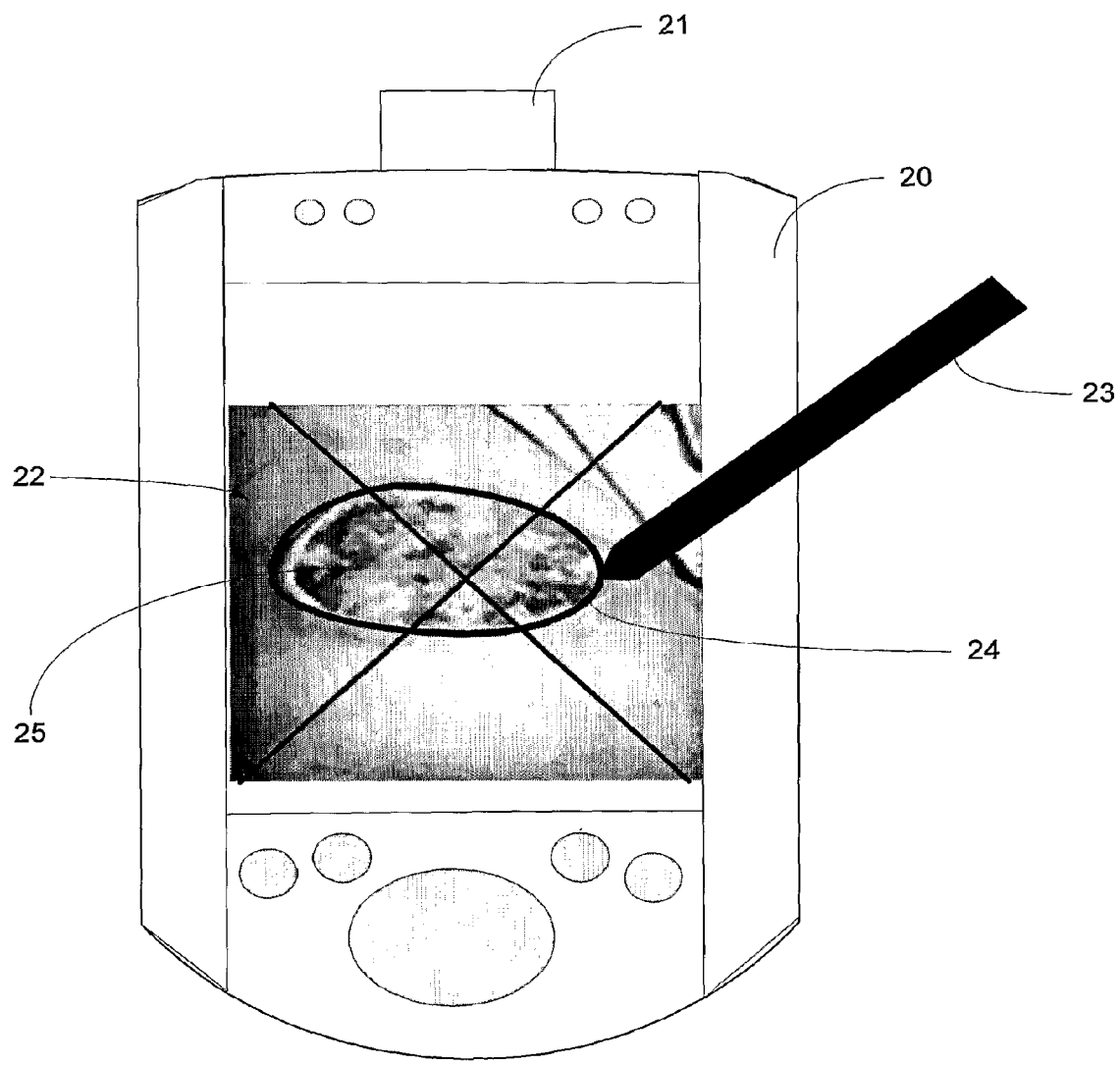
FIG. 5 shows one embodiment employing a personal digital assistant (PDA) for performing methods of the invention.

Apparatus for performing the method may take a variety of forms ranging from a stationary system (having a stationary camera or a handheld camera connected wirelessly or by a cable) to a fully portable unit. Portable units in the form of PDAs, cell phones, notebooks, ultramobile PCs etc. including an integrated or plug-in camera allow great flexibility, especially for medical services outside of hospitals. Referring now to FIG. 5 an apparatus for implementing the invention according to one exemplary embodiment is shown. The apparatus consists of a PDA 20 including a camera, such as a Palm or HP iPaQ, having a cross hair laser generator 21 which projects cross hairs at an angle to the optical axis of the PDA camera (as shown in FIG. 1). For this embodiment the cross hair laser generator may be offset from the camera by about 50 millimeters and disposed at an angle of about 30° to the optical axis of the camera. An image is captured by the camera of the PDA and displayed by touch screen 22. A user can draw an outline 24 about the boundary of the wound 25 using input device 23 on touch screen 22. The apparatus may allow adjustment of outline 24 using input device 23.

In one embodiment placing input device 23 near outline 24 and dragging it may drag the proximate portion of the outline as the input device 23 is dragged across the screen. This may be configured so that the effect of adjustment by the input device is proportional to the proximity of the input device to the outline. Thus, if the input device is placed proximate to the outline the portion proximate to the outline will be adjusted whereas if the input device is placed some distance from the outline a larger area of the outline will be adjusted as the input device is dragged.

Utilising manual input of the outline avoids the need for complex image processing capabilities and allows a compact portable unit, such as a PDA, to be utilised. Further, this approach utilises human image processing capabilities to determine the outline where automated approaches may be less effective.

Once an image is captured it may be stored by the PDA in a patient record along with measurement information (wound area, wound depth, wound volume etc). An image without the cross hairs may also be captured by the PDA deactivating laser 21. This may be desirable where an image of the wound only is required. Where previous information has been stored comparative measurements may be made and an indication of improvement or deterioration may be provided. Where the PDA has wireless capabilities images may be sent directly for storage in a central database or distributed to medical professionals for evaluation. This allows an expert to review information obtained in the field and provide medical direction whilst the health practitioner is visiting the patient. The historic record allows patient progress to be tracked and re-evaluated, if necessary.

Measurements of other wound information may also be made. The colour of the wound and the size of particular coloured regions may also be calculated. These measurements may require a colour reference target to be placed within the image capture area for accurate colour comparison to be made.

Figure 6:
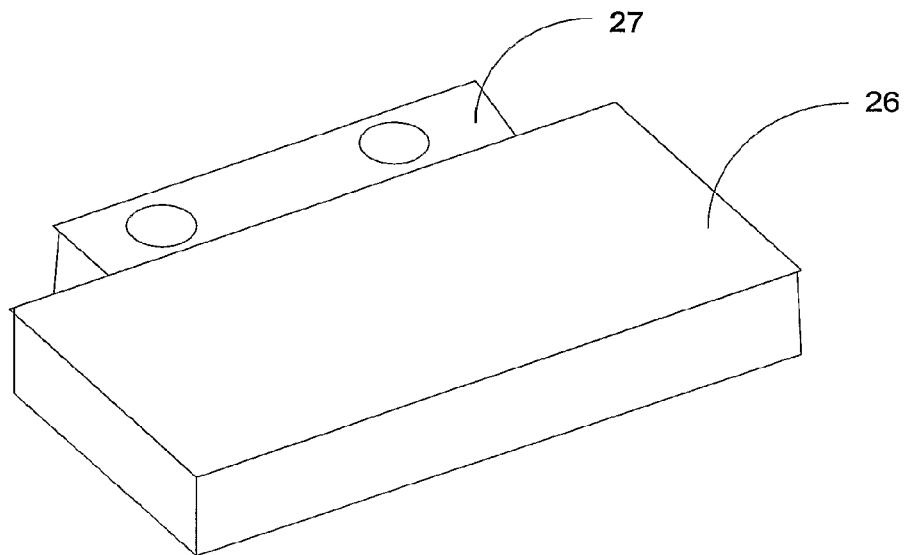
FIG. 6 shows a bottom view of a Tablet PC and 3-D camera.
Figure 7:
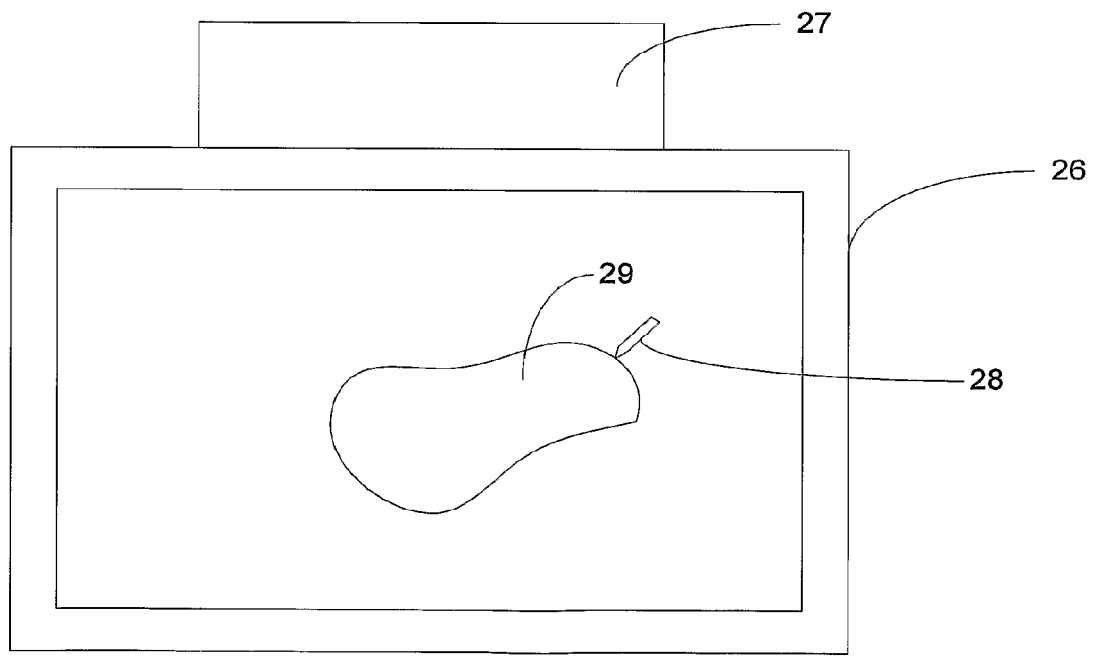
FIG. 7 shows a top view of the Tablet PC and 3-D camera of FIG. 6.

According to another embodiment a 3-D camera may be employed. FIGS. 6 and 7 show a tablet PC 26 having a stereoscopic 3-D camera 27 connected thereto. Tablet PC 26 is a notebook PC with an interactive screen such as a Toshiba Portege M200 and camera 27 may be a stereo camera such as a Point-Grey Bumblebee camera. In this embodiment the stereoscopic camera 27 provides three-dimensional image information which is utilised by the tablet PC 26 to produce a three-dimensional model. However, as in the previous embodiments, a user utilising input device 28 may draw outline 29 around the wound displayed on the tablet PC screen. Utilising the three dimensional data, area and volume may be directly calculated.

In other embodiments "time-of-flight" cameras may be substituted for camera 27. Time-of-flight cameras utilise modulated coherent light illumination and per-pixel correlation hardware.

Figure 8:
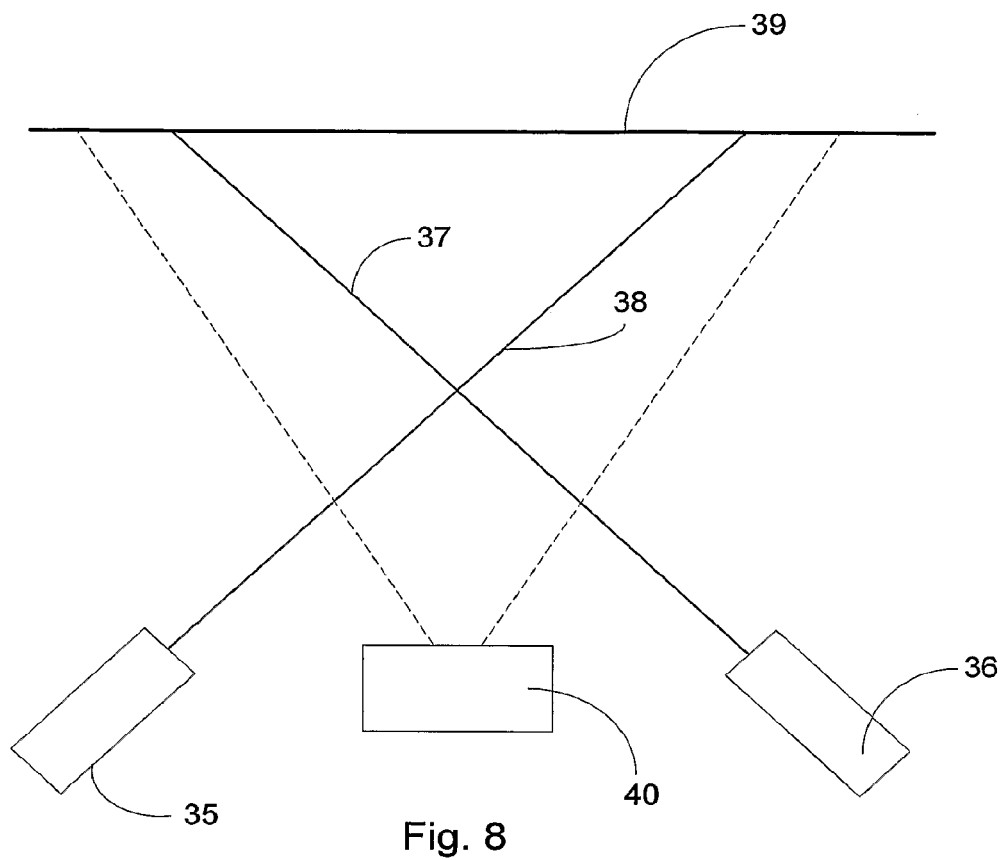
FIG. 8 shows an alternative apparatus and method.
Figure 9:
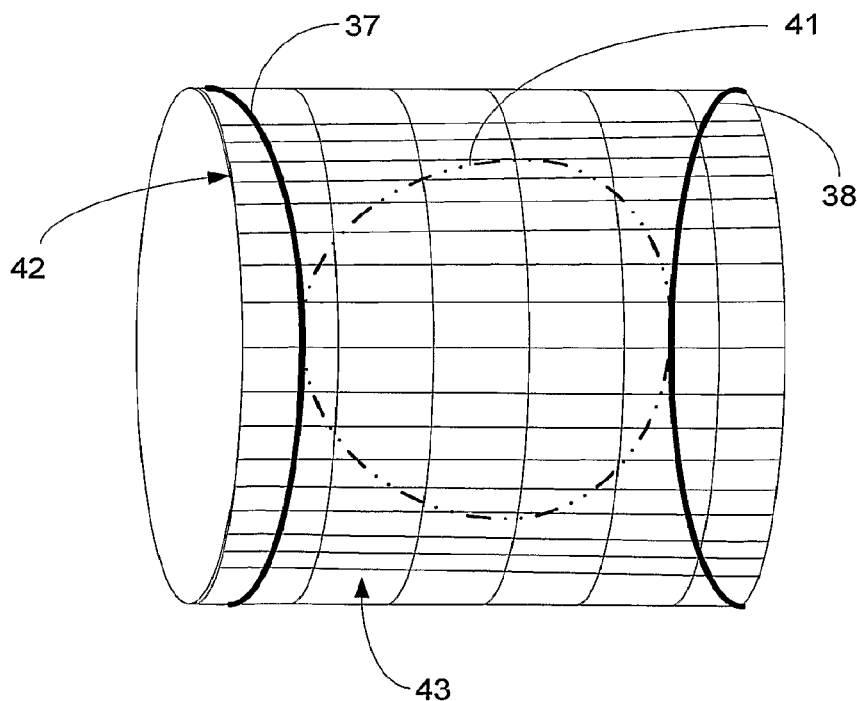
FIG. 9 shows an image illustrating a method of using the apparatus of FIG. 8.

Referring now to FIGS. 8 and 9 an alternative apparatus and method will be described. The apparatus shown in FIG. 8 includes a pair of lasers 35 and 36 which project crossing fan beams 37 and 38 onto surface 39. Lasers 35 and 36 are maintained in a fixed relationship with respect to each other and camera 40. By utilising crossing beams 37 and 38 the spacing between beams 37 and 38 may be adjusted by a user over a convenient range by moving the assembly of lasers 35, 36 and camera 40 towards or away from surface 39.

FIG. 9 illustrates use of the apparatus shown in FIG. 8 in relation to a cylindrical surface 42, such as is typical for a section of an arm or leg. The method may be applied to any surface that may be transformed to a planar (flat) form, ie "unwrapped". In the case of a "developable" surface, there is no distortion and the surface remains continuous, by definition. When fan beams 37 and 38 are projected onto cylindrical surface 42 they curve in a diverging manner as shown in FIG. 9. A user moves the assembly of lasers 35 and 36 and camera 40 with respect to the surface 42 so as to place beams 37 and 38 just outside the boundary 41 of a wound. Camera 40 then captures an image as shown in FIG. 9. For larger wounds the beams 37 and 38 may be within the boundary 41 of a wound.

The three-dimensional locations of elements of beams 37 and 38 may then be determined from the captured image. A three dimensional model of the surface (grid 43 illustrates this) may be calculated using the three dimensional coordinates of elements along lines 37 and 38. The model may be an inelastic surface draped between the three-dimensional coordinates of the structured light elements, or an elastic surface stretched between the three-dimensional coordinates, or a model of the anatomy, or simply a scaled planar projection. A model of the anatomy may be a model retrieved from a library of models, or simply a geometric shape approximating anatomy (a cylinder approximating a leg, for example).

In a first method the three dimensional surface may be unwrapped to form a planar image in which all regions have the same scale (i.e. for a grid the grid is unwrapped such that all cells of the image are the same size). The area within wound boundary 41 may then be easily calculated by calculating the area from the planar image.

Alternatively the area within wound boundary 41 may be calculated by scaling the areas within each region according to scale attributes associated with each region (e.g. for the grid example normalising the total area within each cell to be the same). The granularity can of course be adjusted depending upon the accuracy required.

This approach could be extended so that a plurality of parallel crossing lines are projected to achieve greater accuracy. The lines could have different optical characteristics (e.g. colour) to enable them to be distinguished. However, the two line approach described above does have the advantage of mimicking some manual approaches currently employed which involves tracing the wound outline onto a transparent sheet and then calculating the area.

Figure 10:
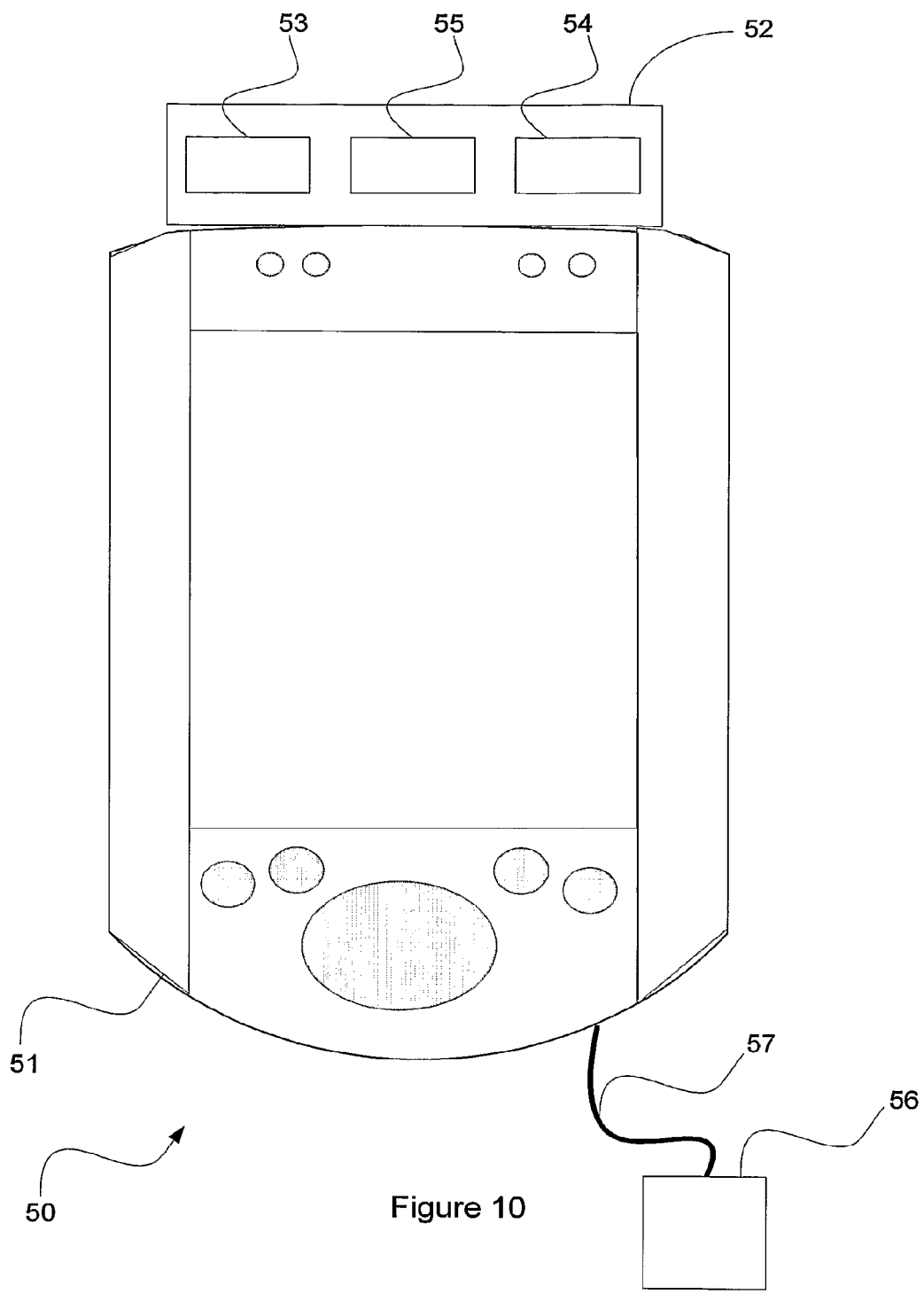
FIG. 10 shows an apparatus according to a further embodiment.

FIG. 10 shows an apparatus according to a further embodiment, in which one or more further sensors are provided. The apparatus 50 includes a PDA 51, with a housing 52 containing a camera 53, laser generator 54 and a GPS receiver 55. The GPS receiver may alternatively be provided in a separate module, within the PDA 51 or in a plugin card. When external to the PDA, the positioning module may be connected to the PDA via any suitable wired or wireless connection. Positioning systems other than GPS may also be suitable.

Use of a positioning system allows automation of tasks and validation of actions. This may be achieved using the apparatus alone, or through communication with a central computer system and database. For example, a nurse may be using the apparatus to monitor wound healing for a patient. The nurse arrives at the patient's home and the position of the home is determined using the GPS system. The position may be used in determining an address. This may be used to ensure that the nurse is at the correct address, possibly by comparison with a schedule of patient visits.

In response to determination of an address, the system may automatically select a patient associated with that address from a patient database. Alternatively, for a new patient, the nurse enters patient information using the PDA and this information is automatically associated with the address determined using the GPS receiver. This avoids the necessity to enter a large amount of data using the PDA. Similarly, the position may be used directly without converting to an address, to select a patient associated with that position, or to associate a new patient with a position.

The positioning system may also be used in auditing user actions. For example, a nurse may enter patient information and this may be verified using the position data by checking it against a patient database. This also allows an employer to monitor staff actions, to ensure that a staff member has in fact visited a particular address or patient.

Data gathered using the GPS system may also be stored for future reference. For example, travel data may be gathered by monitoring position information over a period of time. This data may be used later in estimating travel times between sites and in establishing or optimizing travel schedules for workers.

FIG. 10 also shows an auxiliary sensor 56, connected to the PDA via a wired connection 57. A wireless connection may also be used and any number of auxiliary sensors may be connected to the PDA. Auxiliary sensors could also be included in the module 52. The auxiliary sensor allows further data to be gathered. For example, where the apparatus is used to capture an image of a wound in a patient's skin, the auxiliary sensor will allow measurement of another physical or chemical parameter associated with the patient, such as temperature, pH, moisture or odour. The auxiliary sensor may also be an optical probe, which illuminates the skin or wound and analyses the spectrum of scattered light. For example, a fluorescence probe could be used.

In one embodiment the auxiliary sensors include a Doppler Ultrasound Probe. The management of some types of wound, such as vascular ulcers, requires measurement of blood-flow in the underlying tissue and Doppler Ultrasound is the method generally used to perform this measurement. Low-power Doppler Ultrasound Probes such as those used in foetal heart-beat monitors may be suitable. This would make it unnecessary for a patient to visit a clinic or hospital, or for a separate ultrasound machine to be transported.

Data gathered from the auxiliary sensors may be associated with a particular address, patient or image. Data may be displayed on the PDA's screen, and may be overlaid on the associated image. The combined information may enable more advanced wound analysis methods to be employed.

Use of auxiliary sensors allows many measurements to be more easily performed at the same time as an image is captured and by the same person. (In a medical setting, this person may also be performing wound treatment.) This is efficient and also allows data to be easily and accurately associated with a particular image or patient.

In any of the above embodiments the section containing the lasers and camera could be combined so that they can be housed in a detachable unit from the PDA, interfaced via a SDIO or Compact Flash (CF) slot, for example. This allows added convenience for the user, plus enables lasers and cameras to be permanently mounted with respect to each other, for ease of calibration. Furthermore, the camera can be optimally focussed, and an illumination means, such as a white LED, may be used to give relatively constant background lighting.

In any of the above embodiments the section containing the camera and/or lasers could be movable with respect to the PDA (being interconnected by a cable or wirelessly). This allows independent manipulation of the camera to capture wounds in awkward locations whilst optimising viewing of the image to be captured.

In any of the embodiments described above, multiple images may be captured in rapid succession. This is particularly advantageous where structured light (e.g. a laser) is used. For example, two images may be captured: one with the laser on and one with the laser off. Subtracting one of these images from the other yields an image with just the laser lines (disregarding the inevitable noise). This facilitates the automated detection of the laser profiles. Other combinations of images may also be useful. For example, three images could be captured: one without illumination but with the laser on, one without illumination and with the laser off and a third image with the illumination on and the laser off. The first two images could be used to detect the laser profile, while the third image is displayed to the user. The first image, showing the laser line with the illumination off would have a higher contrast, so that the laser line would stand out more clearly. Capturing the images in rapid succession means that the motion of the camera between the images is negligible.

Figure 11:
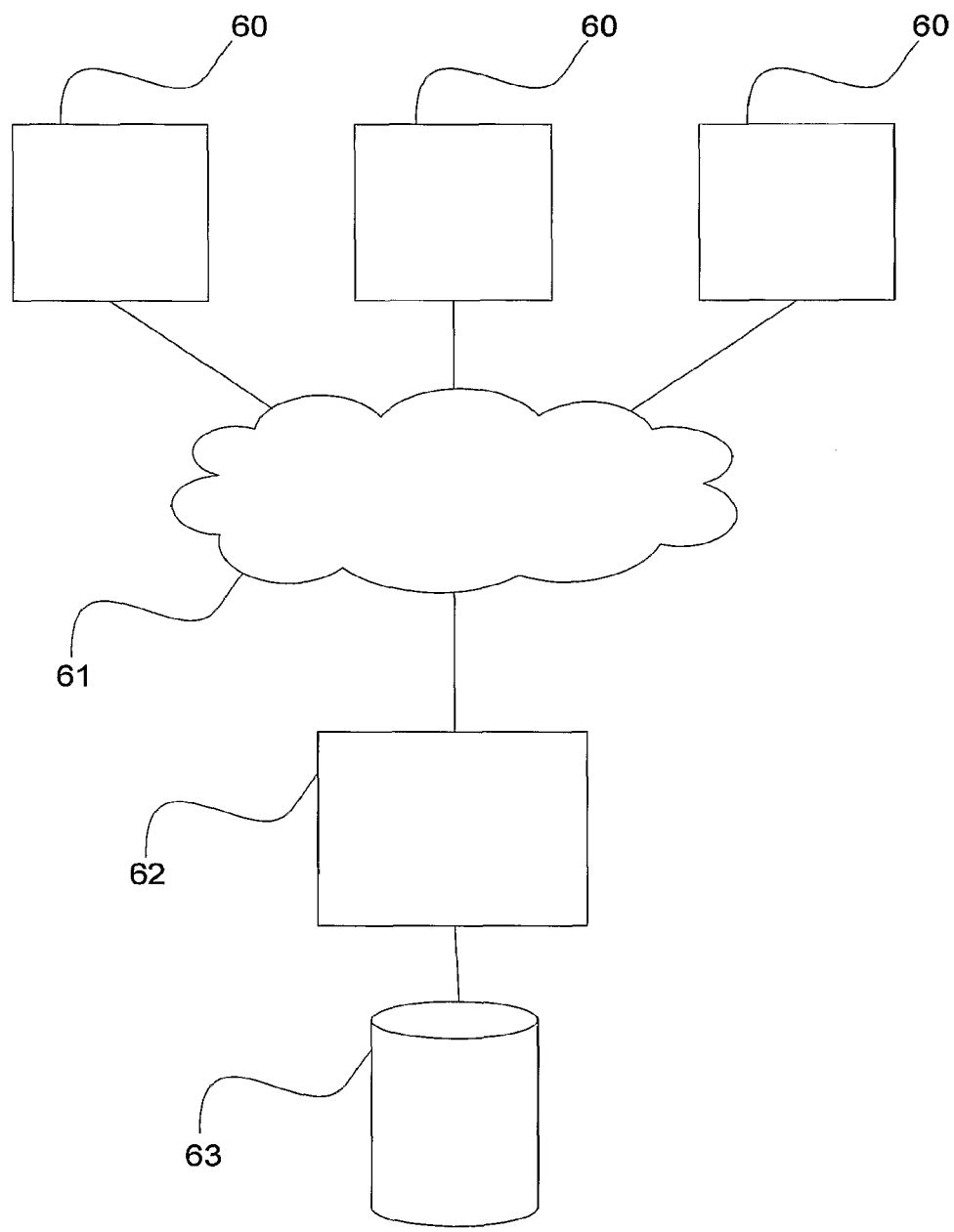
FIG. 11 shows a system according to another embodiment.

FIG. 11 shows a system including one or more portable apparatuses 60 such as those described above. These apparatuses 60 may communicate via a communication network 61 with a central server 62. Preferably the apparatuses 60 communicate wirelessly with the server 62. The central server 62 may utilise an external database 63 for data storage.

This centralised system allows appropriate categorising and storage of data for future use. For example, by mining historical data from the database it is possible to analyse the efficacy of a particular treatment or to compare different treatments. Statistical trends of conditions, treatments and outcomes can be monitored. This data can be used to suggest a particular treatment, based on a set of symptoms exhibited by a particular patient. Data can provide predictions for wound healing. Where actual healing differs from the prediction by more than a threshold, the system may issue an alert.

A healthcare provider can use the data to audit efficiency of its whole organisation, departments within the organisation or even individual workers. Historical data may be compared with historical worker schedules to determine whether workers are performing all tasks on their schedules. Efficiencies of different workers may be compared.

There are thus provided methods of measuring wounds that are simple, inexpensive, repeatable and may be performed remotely. The methods utilise human image processing capabilities to minimise the processing requirements.

The methods do not require the placement of articles near the wound and allow historical comparison of a wound. The apparatus are portable with relatively low processing requirements and enable records to be sent wirelessly for evaluation and storage.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

The invention claimed is:

1. A portable apparatus including:
   a. a camera for capturing an image of a surface feature;
   b. a portable computing device including a processor adapted to determine a scale associated with the image; and
   a. a positioning module allowing the position of the apparatus to be determined.

2. A portable apparatus as claimed in claim 1 wherein the positioning module includes a GPS receiver.

3. A system including a portable apparatus as claimed in claim 1, the system being configured to determine the position of the apparatus using the positioning module and to retrieve personal details associated with the position.

4. A system as claimed in claim 3 configured to associate the image with the address and/or position and/or personal details.

5. A portable apparatus as claimed in claim 1 wherein the portable computing device communicates via a wireless connection with the positioning module.

6. A portable apparatus as claimed in claim 5 wherein the positioning module is located in a separate housing physically connected to the portable computing device.

7. A system including a portable apparatus as claimed in claim 1, the system being configured to determine the position of the apparatus using the positioning module and to determine address information in accordance with the position.

8. A portable apparatus as claimed in claim 1 wherein the surface feature is a dermatological surface feature.

9. A system as claimed in claim 1 configured to monitor movement of the portable apparatus over a period of time and to store travel data in a database.

10. A system as claimed in claim 9 configured to retrieve travel data from the database for use in determining a travel schedule for a user of the portable apparatus.

11. A system as claimed in claim 1 including one or more structured light projectors configured to project structured light onto the surface, the structured light including two or more structured light components, each projected at a different angle to the camera's optical axis.

12. An apparatus as claimed in claim 11 wherein the structured light components are spots projected onto the surface.

13. An apparatus as claimed in claim 11 wherein the structured light components are stripes projected onto the surface.

14. An apparatus as claimed in claim 11 wherein the structured light includes more than two structured light components.

15. A healthcare apparatus including:
   a. a camera for capturing an image of a surface feature on a patient;
   b. one or more auxiliary sensors for determining a physical or chemical parameter associated with the patient; and
   c. a portable computing device configured to receive image data from the camera and output from the auxiliary sensors, including a processor adapted to determine a scale associated with the image.

16. A healthcare apparatus as claimed in claim 15 wherein the auxiliary sensors include one or more of: a Doppler Ultrasound Probe; a thermometer; a pH sensor; a moisture sensor; an odor sensor; and an optical probe.

17. A healthcare apparatus as claimed in claim 15 including a portable computing device and a separate module containing the camera and connected to the portable computing device, wherein at least some of the auxiliary sensors are also included in the separate module.

18. A healthcare apparatus as claimed in claim 15 configured to associate the output of the auxiliary sensors with the image.

19. A healthcare apparatus as claimed in claim 15 configured to associate the output of the auxiliary sensors with the patient.

20. A healthcare apparatus as claimed in claim 15 wherein the one or more auxiliary sensors include a temperature sensor.

21. A healthcare apparatus as claimed in claim 15 wherein the one or more auxiliary sensors include a pH sensor.

22. A healthcare apparatus as claimed in claim 15 wherein the one or more auxiliary sensors include a moisture sensor.

23. A healthcare apparatus as claimed in claim 15 wherein the one or more auxiliary sensors include an odor sensor.

24. A healthcare apparatus as claimed in claim 15 wherein the one or more auxiliary sensors include an optical spectral analysis probe.

25. A healthcare apparatus as claimed in claim 15 wherein the one or more auxiliary sensors include a fluorescence probe.

26. A healthcare apparatus as claimed in claim 15 wherein the one or more auxiliary sensors include a Doppler ultrasound probe.

* * * * *